United States Patent [19]
Olsson et al.

[11] Patent Number: 5,278,150
[45] Date of Patent: Jan. 11, 1994

[54] 2-HYDRAZOADENOSINES AND THEIR UTILITY FOR THE TREATMEAT OF VASCULAR CONDITIONS

[75] Inventors: Ray A. Olsson, Tampa; Robert D. Thompson, Riverview, both of Fla.

[73] Assignee: Whitby Research, Inc., Richmond, Va.

[21] Appl. No.: 873,440

[22] Filed: Apr. 24, 1992

[51] Int. Cl.$^5$ .................... A61K 31/70; C07H 19/167
[52] U.S. Cl. .................................. 514/46; 536/27.61
[58] Field of Search ................. 536/26, 27.61; 514/46

[56] References Cited

U.S. PATENT DOCUMENTS

| | | | |
|---|---|---|---|
| 3,819,613 | 6/1974 | Marumoto et al. | 536/26 |
| 4,140,851 | 2/1979 | Townsend | 536/24 |
| 4,224,438 | 9/1980 | Fauland et al. | 536/26 |
| 5,053,499 | 10/1991 | Kojima et al. | 536/24 |
| 5,155,098 | 10/1992 | Effland et al. | 514/46 |

FOREIGN PATENT DOCUMENTS 2034785  1/1972  Fed. Rep. of Germany .

*Primary Examiner*—Johnnie R. Brown
*Assistant Examiner*—L. Eric Crane
*Attorney, Agent, or Firm*—Richard J. Hammond

[57] ABSTRACT

The present invention discloses a compound of the formula:

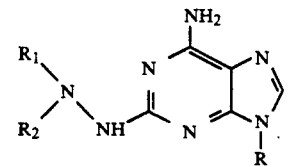

where $R_1$ is hydrogen or the group

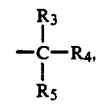

where $R_3$ and $R_4$ are the same or different and are hydrogen, $C_1$ to $C_{12}$ linear or branched alkyl, $C_3$ to $C_7$ cycloalkyl, $C_6$ to $C_{10}$ aryl unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_2$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a monosaccharide radical selected from the group consisting essentially of glucose, fructose, ribose, 2-deoxyribose, mannose, galactose, xylose and arabinose.

28 Claims, No Drawings

2-HYDRAZOADENOSINES AND THEIR UTILITY FOR THE TREATMEAT OF VASCULAR CONDITIONS

FIELD OF THE INVENTION

The present invention relates to the synthesis and utility of 2-substituted adenosines. More particularly, this invention relates to the preparation of 2-hydrazeno adenosines and their use as $A_2$ receptor agonists.

BACKGROUND OF THE INVENTION

Adenosine (9-$\beta$-D-ribofuranosyl-9H-purin-6-amine) was characterized in the late '20s as having hypotensive and bradycardia activity. Since then, considerable research in the molecular modification of adenosine has led to the general conclusion that cardiovascular activity is limited to analogs having intact purine and $\beta$-ribofuranosyl rings.

Further research more clearly defined how the activity of these adenosine analogs affected the purinergic receptors in peripheral cell membranes, particularly the $A_1$ and $A_2$ receptors.

High selectivity combined with significant affinity at the $A_2$ receptor in rat membranes was observed for certain adenosine amines bearing a two-carbon chain to which was attached an aryl, heteroaryl, or alicyclic moiety. 2-(2-Phenethylamino)adenosine, a 14-fold $A_2$ selective compound, was modified by introduction of a variety of substituents in the benzene ring and in the side chain. Some of these changes led to improved $A_2$ affinity and increased selectivity. Replacement of the phenyl moiety by a cyclohexenyl group produced a 210-fold selective agonist, whereas the cyclohexanyl analog was 530-fold selective at the $A_2$ site. These compounds showed hypotensive activity in rat models over a range of doses without the bradycardia observed with less selective agonists. See Francis et al., *J. Med. Chem.*, 34 2570-2579 (1991).

A series of 2-alkoxyadenosines were prepared and tested for agonist activity at the $A_1$ and $A_2$ adenosine receptors of the atrioventricular node and coronary arteries (vasodilation). Activities at the $A_1$ receptor site were low and did not show a clear relationship to the size or hydrophobicity of the C-2 substituent. All the analogs were more potent at the $A_2$ receptor, activity varying directly with the size and hydrophobicity of the alkyl group. The most potent analog in this series, 2-(2-cyclohexylethoxy)adenosine, had an $EC_{50}$ of 1 nM for coronary vasodilation and was 8700-fold selective for the $A_2$ receptor. See Ueeda et al., *J. Med. Chem.*, 34 (4) 1334-1339 (1991).

It has now been discovered that 2-hydrazono-adenosines display superior selectivity as coronary vasodilators and $A_1AR$ agonists.

DESCRIPTION OF THE PREFERRED EMBODIMENTS

The compounds of the present invention have the following formula:

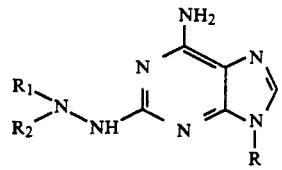

where $R_1$ is hydrogen or the group

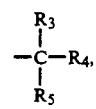

where $R_3$ and $R_4$ are the same or different and are hydrogen, $C_1$ to $C_{12}$ linear or branched alkyl, $C_3$ to $C_7$ cycloalkyl, $C_6$ to $C_{10}$ aryl unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_7$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a monosaccharide radical selected from the group consisting of glucose, fructose, ribose, 2-deoxyribose, mannose, galactose, xylose and arabinose.

In the compounds of the present invention, it is preferred that $R_1$ is

where $R_2$ is taken together with $R_5$ to form a chemical bond, i.e., the preferred compounds of the present invention are those of the formula:

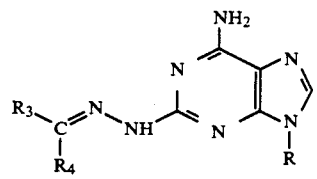

where $R_1$, $R_3$ and $R_4$ are defined above.

In the compounds of formula II, it is preferred that $R_4$ is hydrogen or ethyl we have made and tested SHA-202, which $R_3=R_4=$ethyl and $R_3$ is ethyl, $C_3$ to $C_7$ cycloalkyl (e.g., cyclohexyl), $C_6$ and $C_{10}$ aryl unsubstituted (phenyl, 1-naphthyl or 2-naphthyl) or substituted with at least one $C_1$ to $C_6$ linear or branched alkyl (4-methyl or 3-methyl), halogen (chloro, fluoro, bromo, etc.), $C_1$ to $C_6$ linear or branched alkoxy (4-methoxy or 3-methoxy), nitro (4-nitro or 3-nitro), amino (4-amino or 3-amino) or $C_4$ to $C_8$ heteroaryl where the heteroatom is nitrogen or sulfur (2-pyridyl, 3-pyridyl, 4-pyridyl, 2-thiophenyl, etc.).

The following are illustrative of the compounds of the present invention:
6-amino-2-{2-[(2-naphthyl)methylene]diazanyl}-9-($\beta$-D-ribofuranosyl)-9H-purine;
6-amino-2-{2-[(3-methylphenyl)methylene]diazanyl}-9-($\beta$-D-ribofuranosyl)-9H-purine;

6-amino-2-{2-[(2-pyridyl)methylene]diazanyl}-9-(β-D-ribofuranosyl)-9H-purine;
6-amino-2-{2-[(4-chlorophenyl)methylene]diazanyl}-9-(β-D-ribofuranosyl)-9H-purine;
6-amino-2-{2-[(1-naphthyl)methylene]diazanyl}-9-(β-D-ribofuranosyl)-9H-purine;
6-amino-2-diazanyl-9-(β-D-ribofuranosyl)-9H-purine;
6-amino-2-{2-[(4-fluorophenyl)methylene]diazanyl}-9-(β-D-ribofuranosyl)-9H-purine;
6-amino-2-{2-[(2-thienyl)methylene]diazanyl}-9-(β-D-ribofuranosyl)-9H-purine;
6-amino-2-{2-[(4-methylphenyl)methylene]diazanyl}-9-(β-D-ribofuranosyl)-9H-purine;
6-amino-2-{2-[1-(4-fluorophenyl)ethylidene]diazanyl}-9-(β-D-ribofuranosyl)-9H-purine;
6-amino-2-{2-(phenylmethylene)diazanyl}-9-(β-D-ribofuranosyl)-9H-purine;
6-amino-2-{2-[(cyclohexyl)methylene]diazanyl}-9-(β-D-ribofuranosyl)-9H-purine;
6-amino-2-{2-[(4-nitrophenyl))methylene]diazanyl}-9-(β-D-ribofuranosyl)-9H-purine;
6-amino-2-{2-[(3-aminophenyl)methylene]diazanyl}-9-(β-D-ribofuranosyl)-9H-purine;
6-amino-2-{2-[(4-pyridyl)methylene]diazanyl}-9-(β-D-ribofuranosyl)-9H-purine;
6-amino-2-{2-[(3-pyridyl)methylene]diazanyl}-9-(β-D-ribofuranosyl)-9H-purine;
6-amino-2-{2-[(4-aminophenyl)methylene]diazanyl}-9-(β-D-ribofuranosyl)-9H-purine;
6-amino-2-{2-[1-(phenyl)ethylidene]diazanyl}-9-(β-D-ribofuranosyl)-9H-purine;
6-amino-2-{2-[(4-methoxyphenyl)methylene]diazanyl}-9-(β-D-ribofuranosyl)-9H-purine;
6-amino-2-{2-[(3-nitrophenyl)methylene]diazanyl}-9-(β-D-ribofuranosyl)-9H-purine;
6-amino-2-{2-[(6-methoxy-2-naphthyl)methylene]diazanyl}-9-(β-D-ribofuranosyl)-9H-purine;
6-amino-2-{2-[(2,3-dimethylphenyl)methylene]diazanyl}-9-(β-D-ribofuranosyl)-9H-purine;
6-amino-2-{2-[(2-imidazolyl)methylene]diazanyl}-9-(β-D-ribofuranosyl)-9H-purine;
6-amino-2-{2-[(4-bromophenyl)methylene]diazanyl}-9-(β-D-ribofuranosyl)-9H-purine;
6-amino-2-{2-[(6-methoxy-1-naphthyl)methylene]diazanyl}-9-(β-D-ribofuranosyl)-9H-purine;
6-amino-2-{2-[(3-thienyl)methylene]diazanyl}-9-(β-D-ribofuranosyl)-9H-purine;
6-amino-2-{2-[(4-ethylphenyl)methylene]diazanyl}-9-(β-D-ribofuranosyl)-9H-purine;
6-amino-2-{2-[1-(4-sec-butylphenyl)ethylidene]diazanyl}-9-(β-D-ribofuranosyl)-9H-purine;
6-amino-2-{2-[(cyclopentyl)methylene]diazanyl}-9-(β-D-ribofuranosyl)-9H-purine;
6-amino-2-{2-[(4-ethoxyphenyl)methylene]diazanyl}-9-(β-D-ribofuranosyl)-9H-purine;
6-amino-2-{2-[(3-N-methyl-aminophenyl)methylene]diazanyl}-9-(β-D-ribofuranosyl)-9H-purine;
6-amino-2-{2-[(4-pyrazinyl)methylene]diazanyl}-9-(β-D-ribofuranosyl)-9H-purine;
6-amino-2-{2-[(3-pyrazinyl)methylene]diazanyl}-9-(β-D-ribofuranosyl)-9H-purine;
6-amino-2-{2-[(4-N-methyl-aminophenyl)methylene]diazanyl}-9-(β-D-ribofuranosyl)-9H-purine;
6-amino-2-{2-[1-(4-methylphenyl)ethylidene]diazanyl}-9-(β-D-ribofuranosyl)-9H-purine;
6-amino-2-{2-[(3-furyl)methylene]diazanyl}-9-(β-D-ribofuranosyl)-9H-purine; and
6-amino-2-{2-[(3-indolizinyl)methylene]diazanyl}-9-(β-D-ribofuranosyl)-9H-purine.

The compounds of the present invention are prepared by the procedure illustrated in the following reaction scheme:

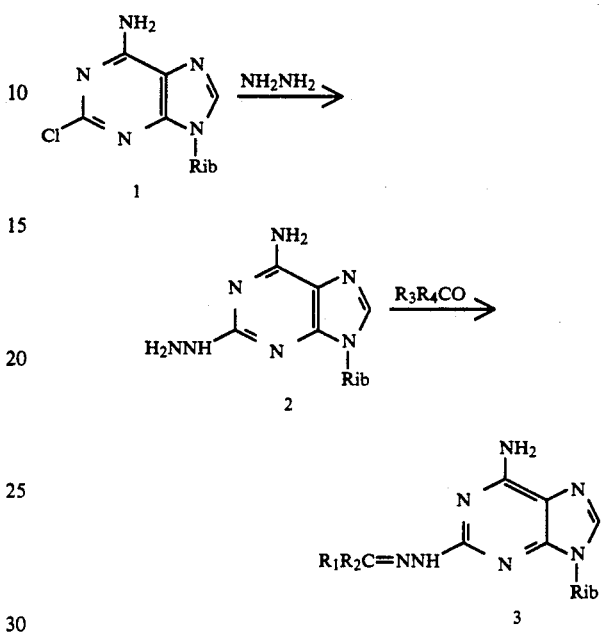

Hydrazine displaces the chloro group of 2-chloroadenosine, 1, readily and in high yield. Thus, aldehydes (where $R_3$ is hydrogen and $R_4$ is one of the groups described previously but not hydrogen), a ketone where $R_3$ and $R_4$ are the same or different and are described previously (but not hydrogen), react with 2-hydrazinoadenosine, 2, under relatively mild conditions, e.g., at room temperature or with moderate heating, to yield hydrazones, 3. The phenylhydrazones are resistant to reduction (e.g., $Na_2S_2O_4$, $NaBH_4$, or low pressure $H_2$ over Pd/C). Separation of the pure compounds is readily accomplished by commercial methods (filtration, recrystallization, etc.)

The compounds prepared by the above route are all therapeutically effective adenosine receptor agonists in mammals. Thus, they are effective for treating conditions which respond to selective adenosine $A_2$ receptor stimulation [(particularly adenosine-2)]. Accordingly, the compounds of the present invention are useful for treating hypertension, thrombosis and atherosclerosis and for causing coronary vasodilation.

*Bioassay Methodology (Ref., J. Med. Chem.* 1991, 34, 1349)

A Langendorff guinea pig heart preparation paced at 260 beats/min. via the left atrium served for assays of $A_1$ adenosine receptor and $A_2$ adenosine receptor agonist activity. The perfusion buffer consisted of 120 mM NaCl, 27 mM $NaHCO_3$, 3.7 mM KCl, 1.3 mM $KH_2PO_4$, 0.64 mM $MgSO_4$, 1.3 mM $CaCl_2$, 2 mM pyruvate, and 5 mM glucose. The buffer was saturated with 95% $O_2$/5% $CO_2$, equilibrated at 37° C. in a heat exchanger and delivered at a pressure equivalent to 55 mm Hg. Continuous drainage of the left ventricle by means of a catheter inserted across the mitral valve insured that this cardiac chamber did no external work. An electrode in the right ventricle monitored the electrocardiogram. Timed collections of cardiac effluent in a graduated cylinder during the steady-state phase of the flow responses to compound administration measured total coronary flow, which was also monitored by an in-line electromagnetic flowmeter in the aortic perfusion cannula. The quotient of the ratio of compound infusion (mol/min) divided by coronary flow rate (L/min) equals agonist concentration in the perfusate. The rate of agonist infusion was increased stepwise at intervals of 3–4 minutes until the appearance of second degree heart block (Wenckebach point). The $EC_{50}$ of prolongation of the stimulus-QRS interval ($EC_{50}$-SQPR), the concentration of compound needed to prolong the interval by 50% of the maximum response, reflects activity at the $A_1$ Adenosine receptor. Logit transformation of the coronary flow data and solution of the regression of logit (coronary flow) on log [compound] for logit=0 yielded an estimate of $EC_{50}$ of coronary vasodilation ($EC_{50}$-CF), an index of $A_2$ adenosine receptor activity. The quotient of the $EC_{50}$ of stimulus-QRS prolongation divided by the $EC_{50}$ of coronary vasodilation provided an index of selectivity. Values of the index >1 indicate selectivity for the $A_2$ adenosine receptor.

EXAMPLES

The following Examples are illustrative only and should not be regarded as limiting the invention in any way.

General Method for the Preparation of 2-(Ar)alkylhydrazinoadenosines

Heating at reflux 1.5 gm. (5.05 mmol) of 2-hydrazinoadenosine and 6.1 mmol of aliphatic aldehyde in 50 ml. methanol resulted in the disappearance of starting material in 2–24 hours, monitored by HPLC. Evaporation of solvent and trituration of the residue with hexane prepared the product for purification by means of medium pressure reverse-phase chromatography [reverse-phase (C-18)HPLC was also used as another method). Isocratic elutions with methanol/water and concentration resulted in pure material. The reaction of aldehydes boiling at less than 65° proceeds at room temperature, going to completion in 24–48 hours. The reaction of aromatic aldehydes proceeded as above; however, when the reaction mixture cooled, the crude product crystallized out of solution. This product was then recrystallized from methanol/water to give the pure product.

EXAMPLE 1

2-[2-(4-Chlorobenzylidene)hydrazino]adenosine 6-amino-2-{2-[4-chlorophenyl)methylene]diazanyl}-9-($\beta$-D-ribofuranosyl)-9H-purine Analysis: Calculated/Found C, 46.63/46.92; N,22.39/22.91; H, 4.60/4.39; Cl, 8.10/8.20.

Yield 85%, Purified: Recrystallized from MeOH/-$H_2O$

NMR (DMSO-$d_6$):3.64–5.43(m, 8H, ribose), 5.86(d, 1H, anomeric), 7.50(m, 4H, $NH_2$ & phenyl H-2 & H-6), 7.86(d, 2H, phenyl H-3 & H-5), 8.20(s, 2H, H-8 & phC$\underline{H}$=NNH), 11.27(br s, 1H, phCH=NN$\underline{H}$).

| Biological Data: | |
| --- | --- |
| $EC_{50}$-CF 4.5 nM | $EC_{50}$-SQPR 14,125 nM |
| Wenckbach 30,374 nM | Selectivity 5,480 (SQPR/CF) |

EXAMPLE 2

2-[2-(4-Fluorobenzylidene)hydrazino]adenosine 6-amino-2-{2-[(4-fluorophenyl)methylene]diazanyl}-9-($\beta$-D-ribofuranosyl)-9H-purine Analysis: Calculated/Found C, 47.44/47.73; N, 22.78/23.09; H, 4.92/4.75; F, 4.41/4.40.

Yield 66%, Purified: Recrystallized from MeOH/-$H_2O$

NMR (DMSO-$d_6$): 3.62–5.62(m, 8H, ribose), 5.90(d, 1H, anomeric), 7.27(m, 4H, $NH_2$ & phenyl H-2 & H-6), 7.86(m, 2H, phenyl H-3 & H-5), 8.17(d, 2H, H-8 & phC$\underline{H}$=NNH), 10.75(br s, 1H, phCH=NN$\underline{H}$).

| Biological Data: | |
| --- | --- |
| $EC_{50}$-CF 2.5 nM | $EC_{50}$-SQPR 12,589 nM |
| Wenckbach 30,903 nM | Selectivity 8,500 (SQPR/CF) |

EXAMPLE 3

2-{2-[(Cyclohexyl)methylene]hydrazino}adenosine 6-amino-2-{2-[(cyclohexyl)methylene]diazanyl}-9-($\beta$-D-ribofuranosyl)-9H-purine Yield 66%, Purified: Recrystallized from MeOH/-$H_2O$ NMR (DMSO-$d_6$):1.00–1.90(m, 10H, cyclohexyl), 2.20(m, 1H, CH—C$\underline{H}$=NNH), 3.55–5.52(m, 8H, ribose), 5.80(d, 1H, anomeric), 6.90(br s, 2H, $NH_2$), 7.23(d, 1H, CH—C$\underline{H}$=NNH), 8.00(s, 1H, H-8), 10.75(br s, 1H, CH—C$\underline{H}$=NN$\underline{H}$).

| Biological Data: | |
| --- | --- |
| $EC_{50}$-CF 0.3 nM | $EC_{50}$-SQPR 3,548 nM |
| Wenckbach 5,922 nM | Selectivity 16,472 (SQPR/CF) |

EXAMPLE 4

2-{2-[(2-Naphthyl)methylene]hydrazino}adenosine 6-amino-2-{2-[(2-naphthyl)methylene]diazanyl}-9-($\beta$-D-ribofuranosyl)-9H-purine Analysis: Calculated/Found C,56.37/56.62; N, 21.91/21 94; H, 5.03/5.07.

Yield 91%, Purified: Recrystallized from MeOH

NMR (DMSO-$d_6$):3.55–5.54(m, 8H, ribose), 5.90(d, 1H, anomeric), 7.18(br s, 2H, $NH_2$), 8.40–8.39(m, 7H, naphthyl), 8.09(s, 2H, H-8 & phC$\underline{H}$=NNH), 10.00(br s, 1H, phCH=NN$\underline{H}$).

| Biological Data: | |
| --- | --- |
| $EC_{50}$-CF 4.2 nM | $EC_{50}$-SQPR 2,615 nM |
| Wenckbach 10,058 nM | Selectivity 767 (SQPR/CF) |

EXAMPLE 5

2-(2-[{3-Pyridyl)methylene]hydrazino}adenosine 6-amino-2-{2-[(3-pyridyl)methylene]diazanyl}-9-($\beta$-D-ribofuranosyl)-9H-purine UV No, $\lambda(\epsilon)$=252 nm (19,700), 291 nm (15,500), 329 nm (24,300)

Yield 82%, Purified: Recrystallized from MeOH/-$H_2O$

NMR (DMSO-$d_6$):3.60–5.60(m, 8H, ribose), 4.88(d, 1H, anomeric), 7.20(br s, 2H, $NH_2$), 7.55(m, 1H, pyridyl H-5), 8.10(d, 2H, H-8 & pydCH=NNH), 8.30–8.92(m, 3H, pryidyl H-2, H-4 & H-6), 10.95 (br s, 1H, pydCH=NNH).

Biological Data:

| $EC_{50}$-CF 15.0 nM | $EC_{50}$-SQPR 32,359 nM |
|---|---|
| Wenckbach 63,460 nM | Selectivity 2,657 (SQPR/CF) |

EXAMPLE 6

2-{2-[(4-Pyridyl)methylene]hydrazino}adenosine 6-amino-2-{2-[(4-pyridyl)methylene]diazanyl}-9-($\beta$-D-ribofuranosyl)-9H-purine UV$\lambda(\epsilon)$=248 nm (17,400), 286 nm (12,900, 335 nm (25,500)

Yield 72%, Purified: Recrystallized from MeOH/-H$_2$O

NMR (DMSO-d$_6$):3.53–5.60(m, 8H, ribose), 5.87(d, 1H, anomeric), 7.12(br s, 2H, NH$_2$), 7.72(d, 2H, pyridyl H-3 & H-5), 8.13(d, 2H, H-8 & pydCH=NNH), 8.62(d, 2H, pyridyl H-2 & H-6), 11.06(br s, 1H, pydCH=NNH).

Biological Data:

| $EC_{50}$-CF 11.0 nM | $EC_{50}$-SQPR 26,607 nM |
|---|---|
| Wenckbach 67,999 nM | Selectivity 2,817 (SQPR/CF) |

EXAMPLE 7

2-[2-(Benzylidene)hydrazino]adenosine 6-amino-2-[2-(phenylmethylene)diazanyl]-9-($\beta$-D-ribofuranosyl)-9H-purine Analysis: Calculated/Found C, 52.27/53.05; N, 24.10/23.87; H, 5.81/5.63.

Yield 70%, Purified: Recrystallized from MeOH/-H$_2$O

NMR (DMSO-d$_6$):3.13–5.62(m, 8H, ribose), 5.82(d, 1H, anomeric), 7.11 (br s, 2H, NH$_2$), 7.28–7.85(m, 5H, phenyl), 8.09(d, 2H, H-8 & phCH=NNH), 10.70(br s, 1H, phCH=NNH).

Biological Data:

| $EC_{50}$-CF 2.3 nM | $EC_{50}$-SQPPR 84,140 nM |
|---|---|
| Wenckbach 216,272 nM | Selectivity 43,347 (SQPR/CF) |

EXAMPLE 8 (COMPARATIVE)

2-Hydrazinoadenosine 6-amino-2-diazanyl-9-($\beta$-D-ribofuranosyl)-9H-purine
UV No, $\lambda(\epsilon)$=258 nm (10,000), 278 nm (9,000)
Yield 86%, Purified: Recrystallized from /H$_2$O Biological Data:

| $EC_{50}$-CF 80.4 nM | $EC_{50}$-SQPR 14,569 nM |
|---|---|
| Wenckbach 18,197 nM | Selectivity 301 (SQPR/CF) |

EXAMPLE 9

2-[2-(4-Methylbenzylidine)hydrazino]adenosine 6-amino-2-{2-[(4-methylphenyl)methylene]diazanyl}-9-($\beta$-D-ribofuranosyl)-9H-purine Analysis: Calculated/Found C, 54.13/54.12; N/24.55/24.40; H, 5.30/5.36.

Yield 75%, Purified: Recrystallized from MeOH/-H$_2$O

NMR (DMSO-d$_6$):2.32(s, 3H, CH$_3$), 3.55–5.58(m, 8H, ribose), 5.86(d, 1H, anomeric), 7.05(br s, 2H, NH$_2$), 7.21(d, 2H, phenyl H-3 & H-5), 7.68(d, 2H, phenyl H-2 & H-6), 8.08(d, 2H, H-8 & phCH=NNH), 10.75(br s, 1H, phCH=NNH).

Biological Data:

| $EC_{50}$-CF 3.3 nmol | $EC_{50}$-SQPPR 39,811 nmol |
|---|---|
| Wenckbach 103,514 nmol | Selectivity 14,144 (SQPR/CF) |

EXAMPLE 10

2-{2-[1-(4-Fluorophenyl)ethylidene]hydrazino}adenosine 6-amino-2-{2- [1-(4-fluorophenyl)ethylidene]diazanyl}-9-($\beta$-D-ribofuranosyl)-9H-purine;

Analysis: Calculated/Found C, 51.80/51.85/; N, 23.49/24.43/; H, 4.83/4.88; F, 4 55/4.64.

Yield 73%, Purified: Recrystallized from MeOH/-H$_2$O

NMR (DMSO-d$_6$):2.22(s, 3H, CH$_3$), 3.53–5.60(m, 8H, ribose), 5.82(d, 1H, anomeric), 7.00(br s, 2H, NH$_2$), 7.21(d, 2H, phenyl H-2 & H-6), 7.90(m, 2H, phenyl H-3 & H-5), 8.04(s, 1H, H-8), 9.20(br s, 1H, phC(CH$_3$)-NNH).

Biological Data:

| $EC_{50}$-CF 3.2 nM | $EC_{50}$-SQPR 4,201 nM |
|---|---|
| Wenckbach 7,300 nM | Selectivity 1,822 (SQPR/CF) |

EXAMPLE 11

2-[2-(4-Methoxybenzylidene)hydrazino]adenosine 6-amino-2-{2-[(4-methoxyphenyl)methylene]diazanyl}-9-($\beta$-D-ribofuranosyl)-9H-purine Analysis: Calculated/Found C, 51.49/51.80; N, 23.35/23.34; H, 5.16/5.54.

Yield 75%, Purified: Recrystallized from MeOH/-H$_2$O

NMR (DMSO-d$_6$):3.54–5.39(m, 8H, ribose), 5.82(d, 1H, anomeric), 6.83–7.20(m, 4H, NH$_2$ & phenyl H-3 & H-5), 7.73(m, 2H, phenyl H-2 & H-6), 8.17(d, 2H, H-8 & phCH=NNH), 10.45(br s, 1H, phCH=NNH).

Biological Data:

| $EC_{50}$-CF 1.7 nM | $EC_{50}$-SQPR 23,000 nM |
|---|---|
| Wenckbach 50,000 nM | Selectivity 14,000 (SQPR/CF) |

EXAMPLE 12

2-{2-[1-Phenyl)ethylidene]hydrazino}adenosine 6-amino-2-{2-[1-(phenyl)ethylidene]diazanyl}-9-($\beta$-D-ribofuranosyl)-9H-purine UV$\lambda(\epsilon)$=247 nm (17,000), 288 sh (18,900), 309 nm (23,100)

Yield 89%, Purified: Recrystallized from MeOH/-H$_2$O

NMR (DMSO-d$_6$):2.32(s, 3H, CH$_3$), 3.51–5.60(m, 8H, ribose), 5.88(d, 1H, anomeric), 7.04(br s, 2H, NH$_2$), 7.45(m, 3H, phenyl H-3, H-4 & H-5), 7.90(m, 2H, phenyl H-2 & H-6), 8.14(s, 1H, H-8), 9.29(br s, 1H, phC(CH$_3$)=NN$\underline{H}$).

| Biological Data: | |
| --- | --- |
| EC$_{50}$-CF 13 nM | EC$_{50}$-SQPR 3,000 |
| Wenckbach 11,000 nM | Selectivity 380 |

EXAMPLE 13

2-{2-[(2-Pyridyl)methylene]hydrazino}adenosine 6-amino-2-{2-[(2-pyridyl)methylene]diazanyl}-9-($\beta$-D-ribofuranosyl)-9H-purine UV$\lambda(\epsilon)$=253 nm (16,300), 285 nm (12,900), 331 nm (25,800)

Yield 85%, Purified: Recrystallized from MeOH/H$_2$O

NMR (DMSO-d$_6$):3.56–5.59(m, 8H, ribose), 5.87(d, 1H, anomeric), 7.15–7.40 (m, 3H, NH$_2$ & pyridyl H-5), 7.70–8.20(m, 4H, pyridyl H-3, H-4, purinyl H-8 and pydC$\underline{H}$=NNH), 8.67(m, 1H, pyridyl H-6), 10.98(br s, 1H, pydCH=NN$\underline{H}$).

| Biological Data: | |
| --- | --- |
| EC$_{50}$-CF 5.7 nM | EC$_{50}$-SQPR |
| Wenckbach 110,000 | Selectivity 42,000 |

EXAMPLE 14

2-{2-[(1-Naphthyl)methylene]hydrazino}adenosine 6-amino-2-{2- [(1-naphthyl)methylene]diazanyl}-9-($\beta$-D-ribofuranosyl)-9H-purine Yield 89%, Purified: Recrystallized from MeOH NMR (DMSO-d$_6$):3.41–5.61(m, 8H, ribose), 5.90(d, 1H, anomeric), 7.18(br s, 2H, NH$_2$), 7.47–8.20(m, 8H, naphthyl, purinyl H-8 and napC$\underline{H}$=NNH), 8.88(s, 1H, naphthyl H-8), 10.89(br s, 1H, napCH=NN$\underline{H}$).

| Biological Data: | |
| --- | --- |
| EC$_{50}$-CF 9.5 nM | EC$_{50}$-SQPR 830 nM |
| Wenckbach 2,000 nM | Selectivity 110 |

EXAMPLE 15

2-{2-[(2-Thienyl)methylene]hydrazino}adenosine 6-amino-2-{2-[(2-thienyl)methylene]diazanyl}-9-($\beta$-D-ribofuranosyl)-9H-purine Yield 76%, Purified: Recrystallized from MeOH/H$_2$O NMR (DMSO-d$_6$):3.47–5.52(m, 8H, ribose), 5.85(d, 1H, anomeric), 7.00–7.60(m, 5H, NH$_2$ & thienyl), 8.05(s, 1H, H-8), 8.30(s, 1H, thienyl C$\underline{H}$=NNH), 10.60(br s, 1H, thienyl CH=NN$\underline{H}$).

| Biological Data: | |
| --- | --- |
| EC$_{50}$-CF 14 nM | EC$_{50}$-SQPR 42,000 nM |
| Wenckbach 93,000 nM | Selectivity 4400 |

EXAMPLE 16

2-[2-(3-Methylbenzylidene)hydrazino]adenosine 6-amino-2-{2-[(3-methylphenyl)methylene]diazanyl}-9-($\beta$-D-ribofuranosyl)-9H-purine Yield 79%, Purified: Recrystallized from MeOH NMR (DMSO-d$_6$):2.32(s, 3H, CH$_3$), 3.54–5.54(m, 8H, ribose), 5.82(d, 1H, anomeric), 7.00–7.73(m, 6H, NH$_2$ & phenyl), 8.08(s, 2H, H-8 & phC$\underline{H}$=NNH), 10.65(br s, 1H, phCH=NN$\underline{H}$).

| Biological Data: | |
| --- | --- |
| EC$_{50}$-CF 4.4 nM | EC$_{50}$-SQPR 17,000 |
| Wenckbach 47,000 nM | Selectivity 4700 |

In a similar manner, the following compounds are prepared:

EXAMPLE 17

2-[2-(4-Nitrobenzylidene)hydrazino]adenosine 6-amino-2-{2-[(4-nitrophenyl)methylene]diazanyl}-9-($\beta$-D-ribofuranosyl)-9H-purine Analysis: Calculated/Found C, 47.55/47.33; N, 26.10/25.89; H, 3.99/4.13.

Yield 79%, Purified: Recrystallized from MeOH

EXAMPLE 18

2-[2-(3-Nitrobenzylidene)hydrazino]adenosine 6-amino-2-{2-[(3-nitrophenyl)methylene]diazanyl}-9-($\beta$-D-ribofuranosyl)-9H-purine Analysis: Calculated/Found C, 47.55/47.36; N, 26.10/26.16; H, 3.99/3.74.

Yield 75%, Purified: Recrystallized from MeOH

EXAMPLE 19

2-[2-(4-Aminobenzylidene)hydrazino]adenosine 6-amino-2-{2-[(4-aminophenyl)methylene]diazanyl}-9-($\beta$-D-ribofuranosyl)-9H-purine

EXAMPLE 20

2-[2-(3-Aminobenzylidene)hydrazino]adenosine 6-amino-2-{2-[(3-aminophenyl)methylene]diazanyl}-9-($\beta$-D-ribofuranosyl)-9H-purine

TABLE
BIOASSAY RESULTS

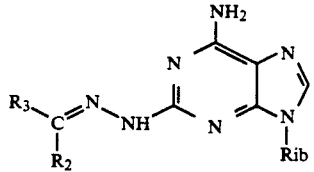

| SUBSTITUENT | | –LOG EC$_{50}$ | |
| --- | --- | --- | --- |
| R$_3$ | R$_4$ | A$_1$ | A$_2$ |
| Ph | H | 4.08 | 8.64 |
| 4-F Ph | H | 4.90 | 8.61 |
| 4-Cl Ph | H | 4.85 | 8.35 |
| 4-MeO Ph | H | 4.64 | 8.76 |
| 4-Me Ph | H | 4.40 | 8.49 |
| 4-F Ph | CH$_3$ | 5.38 | 8.49 |
| 2-Naphthyl | H | 5.58 | 8.38 |
| Cyclohexyl | H | 5.45 | 9.59 |
| 3-Me-1-Bu | H | 4.68 | 9.33 |
| 1-Pent | H | 4.41 | 8.99 |
| 2-C | H | 5.01 | 9.16 |

TABLE-continued
BIOASSAY RESULTS

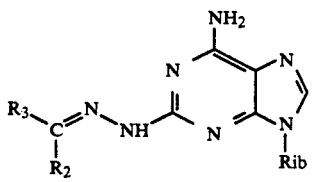

| SUBSTITUENT | | −LOG EC$_{50}$ | |
|---|---|---|---|
| R$_3$ | R$_4$ | A$_1$ | A$_2$ |
| Hexylethyl 3-Ph Propyl | H | 4.18 | 8.71 |
| 3-C Hexylpropyl | H | 4.18 | 8.75 |
| 3-Cyclohexenyl | H | 4.86 | 9.49 |
| *Comparative* | | | |
| Adenosine | | 5.47 | 7.69 |
| 2-Amino-adenosine | | 4.95 | 6.65 |
| 2-Hydrazino-adenosine | | 4.70 | 7.10 |

Ph - phenyl
Rib - ribose

We claim:

1. A compound of the formula:

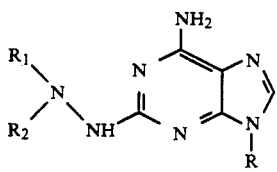

where R$_1$ is hydrogen or the group

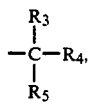

where R$_3$ and R$_4$ are the same or different and are hydrogen, C$_1$ to C$_{12}$ linear or branched alkyl, C$_3$ to C$_7$ cycloalkyl, C$_6$ to C$_{10}$ aryl unsubstituted or substituted with C$_1$ to C$_6$ linear or branched alkyl, C$_1$ to C$_6$ linear or branched alkoxy, nitro, amino, amino substituted with at least one C$_1$ to C$_6$ linear or branched alkyl or phenyl, C$_7$ to C$_{10}$ aralkyl, C$_4$ to C$_8$ heteroaryl wherein said heteroatom is nitrogen, phosphorous, sulfur or oxygen, and R$_2$ is hydrogen, or taken together with R$_5$, forms a chemical bond, and R is a ribose radical.

2. The compound according to claim 1, wherein R$_1$ is the group

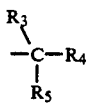

and R$_2$ taken together with R$_5$ is a chemical bond, and R$_3$ and R$_4$ are as defined in claim 1.

3. The compound according to claim 2, wherein R$_4$ is hydrogen or methyl.

4. The compound according to claim 3, wherein R$_3$ is C$_3$ to C$_7$ cycloalkyl.

5. The compound according to claim 4, wherein R$_3$ is cyclohexyl.

6. The compound according to claim 3, wherein R$_3$ is C$_6$ to C$_{10}$ aryl unsubstituted.

7. The compound according to claim 6, wherein R$_3$ is phenyl, 1-naphthyl or 2-naphthyl.

8. The compound according to claim 3, wherein R$_3$ is C$_6$ to C$_{10}$ aryl substituted with at least one C$_1$ to C$_6$ linear or branched alkyl.

9. The compound according to claim 8, wherein said alkyl is 4-methyl.

10. The compound according to claim 8, wherein said alkyl is 3-methyl.

11. The compound according to claim 3, wherein R$_3$ is C$_6$ to C$_{10}$ aryl substituted with at least one halogen.

12. The compound according to claim 11, wherein said halogen is 4-chloro.

13. The compound according to claim 12, wherein said halogen is 4-fluoro.

14. The compound according to claim 3, wherein R$_3$ is C$_6$ to C$_{10}$ aryl substituted with at least one C$_1$ to C$_6$ linear or branched alkoxy.

15. The compound according to claim 14, wherein said alkoxy is 4-methoxy.

16. The compound according to claim 3, wherein R$_3$ is C$_6$ to C$_{10}$ aryl substituted with at least one nitro.

17. The compound according to claim 16, wherein said nitro is 4-nitro.

18. The compound according to claim 16, wherein said nitro is 3-nitro.

19. The compound according to claim 3, wherein R$_3$ is C$_6$ to C$_{10}$ aryl substituted with at least one amino.

20. The compound of claim 3 wherein, R$_3$ is C$_4$ to C$_8$ heteroaryl wherein said heteroatom is nitrogen or sulfur.

21. The compound according to claim 3, wherein said heteroaryl is 3-pyridyl.

22. The compound according to claim 3, wherein said heteroaryl is 4-pyridyl.

23. The compound according to claim 3, wherein said heteroaryl is 2-pyridyl.

24. The compound according to claim 3, wherein said heteroaryl is 2-thienyl.

25. The compound according to claim 19 wherein R$_3$ is phenyl substituted with 4-amino.

26. The compound according to claim 19 wherein R$_3$ is phenyl substituted with 3-amino.

27. A method for causing coronary vasodilation in a mammal requiring such vasodilation by administering to said mammal an effective amount of a compound of the formula:

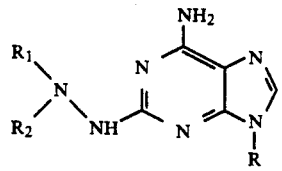

where R$_1$ is hydrogen or the group

where R$_3$ and R$_4$ are the same or different and are hydrogen, C$_1$ to C$_{12}$ linear or branched alkyl, C$_3$ to C$_7$ cycloalkyl, C$_6$ to C$_{10}$ aryl unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_7$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a ribose radical.

28. A method for treating hypertension, thrombosis and atherosclerosis, which comprises administering to a mammal in need of such treatment an effective amount of a compound of the formula:

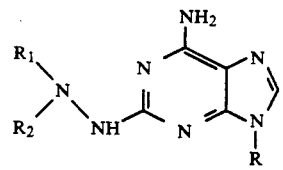

where $R_1$ is hydrogen or the group

where $R_3$ and $R_4$ are the same or different and are hydrogen, $C_1$ to $C_{12}$ linear or branched alkyl, $C_3$ to $C_7$ cycloalkyl, $C_6$ to $C_{10}$ unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_7$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a ribose radical.

* * * * *